(12) United States Patent
Jochum et al.

(10) Patent No.: US 7,590,500 B2
(45) Date of Patent: Sep. 15, 2009

(54) SYSTEM FOR HIGH DYNAMIC RANGE ANALYSIS IN FLOW CYTOMETRY

(75) Inventors: Theodore W. Jochum, Fort Collins, CO (US); Daniel N. Fox, Fort Collins, CO (US); Thomas L. Thrasher, Fort Collins, CO (US); George Malachowski, Melbourne (AU)

(73) Assignee: Beckman Coulter, Inc., Fullerton, CA (US)

( * ) Notice: Subject to any disclaimer, the term of this patent is extended or adjusted under 35 U.S.C. 154(b) by 189 days.

(21) Appl. No.: 10/587,887

(22) PCT Filed: Feb. 28, 2005

(86) PCT No.: PCT/US2005/006380

§ 371 (c)(1),
(2), (4) Date: Jul. 27, 2006

(87) PCT Pub. No.: WO2005/091893

PCT Pub. Date: Oct. 6, 2005

(65) Prior Publication Data

US 2007/0124089 A1    May 31, 2007

Related U.S. Application Data

(60) Provisional application No. 60/550,240, filed on Mar. 3, 2004.

(51) Int. Cl.
*G01D 18/00* (2006.01)
(52) U.S. Cl. ............... 702/85; 702/120; 341/143; 356/28; 356/39
(58) Field of Classification Search ............ 702/85, 702/120; 341/143; 356/28, 39
See application file for complete search history.

(56) References Cited

U.S. PATENT DOCUMENTS

| 4,987,539 A | 1/1991 | Moore et al. |
| 5,598,158 A | 1/1997 | Linz |
| 5,675,517 A * | 10/1997 | Stokdijk .................. 702/85 |
| 6,507,391 B2 | 1/2003 | Riley et al. |

* cited by examiner

*Primary Examiner*—Tung S Lau
*Assistant Examiner*—Sujoy K Kundu
(74) *Attorney, Agent, or Firm*—Sterne, Kessler, Goldstein & Fox PLLC.

(57) ABSTRACT

A flow cytometer capable of using electronics to analyze a large dynamic range while avoiding and/or correcting traditional limitations of acquisition electronics. The invention allows for measuring signal characteristics, which may include but are not limited to linear peak, integral, logarithmic peak, and pulse width. Other system parameters may also be generated by the invention to indicate timing or status information. Accurate and precise measurements may be performed by correcting for input errors if needed, and by transforming the input signal to produce a more easily measured form.

16 Claims, 7 Drawing Sheets

SYSTEM FOR HIGH DYNAMIC RANGE ANALYSIS IN FLOW CYTOMETRY

This application is a national phase entry under 35 U.S.C. §371 of PCT/US005/006380, filed on Feb. 28, 2005. Said PCT/US005/006380 claims the benefit of U.S. Provisional Application No. 60/550,240 filed Mar. 3, 2004.

TECHNICAL FIELD

This invention relates to a method and apparatus for the analysis, and possible sorting, of particles, e.g. in a flow cytometer.

BACKGROUND ART

Flow cytometers typically analyze particles by applying a stain or reagent, suspending them within a stream of sheath fluid, and passing the stream linearly through a laser. When the laser strikes the particles, it produces several channels of information in the form of scattered light and emitted light at different wavelengths. Traditionally photo diodes and/or photo multiplier tubes are then used to convert the optical signal into an electronic signal, which may then be measured and characterized. However, depending on particle size, the particular chemicals used, laser power, and many other factors, the signals produced may occupy a large range of magnitudes. A small, unstained particle or "negative" particle may produce a signal with magnitude of only 1/1000th or less than that of a large, stained particle. Furthermore, some systems require analyzing particles at rates of over 50,000 per second, but also possibly as slow as only several per second. Accurate analysis over this large range of magnitudes and event rates has introduced many problems.

Early systems designed to analyze these signals used an analog approach for peak determination of the linear, logarithmic, and integral values during a gated window, and then digitized the peak values at the end of the window. These systems sometimes took an input signal, used a standard base line restoration (BLR) circuit to remove DC offsets, then used a linear amplifier to create the linear value, a logarithmic amplifier to create the logarithmic value, and an integrator circuit to calculate the integral during the window. An analog peak sample and hold circuit (PSH) was sometimes used to find the maximum value during the event, and this maximum value was sometimes then converted with an analog to digital converter (ADC) to get a digital value. The logarithmic amplifier was sometimes used to allow a wider dynamic range of analysis than the linear signal could provide. These types of systems give a good starting point for signal analysis, but have some inherent problems. Some of these problems include:
1. Analog logarithmic amplifiers usually do not have a perfect transfer function and can contain "ripples" that may distort the input signal. Thus, the output can be higher or lower than it should have been depending upon the input magnitude, which introduced errors into calculations and distorted population histograms.
2. Analog PSH circuits can have several problems, such as noise susceptibility, that may add to the inherent error of the system.
3. In some case, especially at very high event rates, the standard BLR circuit may introduce errors of its own. This error, which may manifest itself as a DC bias, may cause pulse distortion as the logarithmic amplifier input crosses from positive to negative and back to positive.

Perhaps to eliminate some of these problems, a second system was developed that eliminated the logarithmic amplifier. In some arrangements this system took the input signal, applied different levels of linear gain, used gated analog PSH, used comparators to determine which range to use, and used a processor to shift the data to the appropriate place. The multiple linear gain stages were sometimes necessary to provide adequate dynamic range.

The second system may sometimes have removed the non-linearity problem of the logarithmic amplifier by not using one. However, these systems did not always eliminate all of the problems, and sometimes introduced some of their own. Some of the problems with this system include:
1. The same analog PSH problems noted above.
2. Transitions from one gain stage to another may not be necessarily perfect, and may create "elbow" effects of non-linear regions.

Perhaps in an attempt to eliminate some of the original problems in a similar manner, a third system was created. In some arrangements, this system may have taken the input signal, may have used ADCs to directly sample the signal, then sometimes may have used a processor to perform digital PSH functionality. A high resolution ADC was sometimes used to achieve the desired dynamic range.

This third system may have removed the non-linearity problem of the logarithmic amplifier, the problems of the analog PSH and the problems of using multiple gain stages. However, this type of system also may have introduced some problems.

The problems with this type of system include analysis dynamic range is sometimes limited to ADC resolution perhaps because the signal is directly sampled. With this system, very high resolution sometimes is required to detect and characterize signals of low magnitude. For example, using a normalized maximum input of 10V to the ADC, to get a fairly standard 12 bits of resolution over 4 decades (80 dB), the ADC may need to have at least 1024 steps in the last decade. In situations where the last decade is a maximum of 10 mV, each step may need to be 10 µV, which may require an ADC with at least 20 bits. Using an ADC with lower resolution could result in quantized, or "picket fence," results. To achieve 5 decades (100 dB), the ADC may need at least 24 bits, and 6 decades (120 dB) may require 27 bits. This may mean that system dynamic range may be limited by ADC technology. To achieve the necessary high resolution, sample speed may need to be given up, which may limit the speed that the signal may be sampled at, which may further limit the speed of overall analysis. A trade-off between analysis rates and resolution then may need to be made, which may make the lower end of the dynamic range quantized.

Prior work for particle analysis electronics in flow cytometry has apparently failed to solve these challenges without introducing new problems. Consequently, there is still a need for analysis electronics that can provide high dynamic range analysis at high event rates.

DISCLOSURE OF INVENTION

Summary of the Invention

The present invention provides a novel system and method for accurately and precisely measuring or characterizing properties of the input signal, especially for a flow cytometer. Signal parameters may be measured or calculated without many of the limitations or errors previously imposed, perhaps providing more accurate data. The invention may alleviate or avoid issues such as, but not limited to, standard BLR error, analog PSH errors, converter or system non-linearities, multi-region "elbow" effects, and high resolution requirements.

These ill effects may be avoided or alleviated with all or portions of the present invention. The invention may prevent standard BLR errors, if needed, by not allowing the BLR to adjust during periods of sample acquisition. The base line may be removed before acquisition or between events and held constant during pulses. If necessary, during high event rates, the base line may be held constant to prevent error from slowly accumulating. If no error is allowed to enter into the system from the BLR circuit, the eventual results may be more accurate and precise.

In some embodiments the present invention may remove converter or system nonlinearities, if needed, by determining the errors and then compensating for them. For example, an analog logarithmic amplifier may be used as a signal converter, but it may contain non-linearities. However, in some embodiments, the invention can provide a means of determining the errors in the transfer function, and a means of applying a correction scheme to reduce or eliminate the error. By removing the non-linearities of the system, result accuracy and precision may again be improved.

In other embodiments, the present invention may separate the required digitization resolution from the sampled dynamic range This may provide a tremendous benefit by allowing an analysis of a much larger dynamic range, and by allowing for flexibility in analyzing different dynamic ranges. Embodiments may accomplish this by applying a non-linear transfer function to the input signal, which may effectively compress a very large dynamic range into a much smaller one by applying greater gains at lower magnitudes. The non-linear transfer function may even be matched to the desired dynamic range and desired response, producing a new signal that may be analyzed at a lower resolution while still providing adequate resolution for the low end of the dynamic range.

In particular, the present invention utilizes an enhanced BLR that may be locked during acquisition to remove any DC offset of an input signal. The baseline corrected signal may then be transformed by a logarithmic amplifier that is, perhaps, calibrated with gain and offset adjustments, and may then be sampled by an ADC and input to a processor. The processor may accept one or more channels of data, with one or more processors per board, and one or more boards per system. This may allow for a flexibility of overall number of channels. The processor may be used to perform the digital PSH function, as well as to calculate or generate any other parameters desired, or provide other needed functionality.

Therefore, by, in part or in combination, eliminating standard BLR errors, removing system or converter non-linearities, and separating digitization resolution from dynamic range, embodiments of the present invention may provide more accurate and precise results for high dynamic ranges and high event rates than previously possible, especially as applied to a flow cytometer.

BEST MODES FOR CARRYING OUT THE INVENTION

The present invention includes a variety of aspects, which may be combined in different ways. The following descriptions are provided to list elements and describe some of the preferred embodiments of the present invention. These elements are listed with initial embodiments. However, it should be understood that they may be combined in any manner and in any number to create additional embodiments. The variously described examples and preferred embodiments should not be construed to limit the present invention to only the explicitly described systems, techniques, and applications. Further, this description should further be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
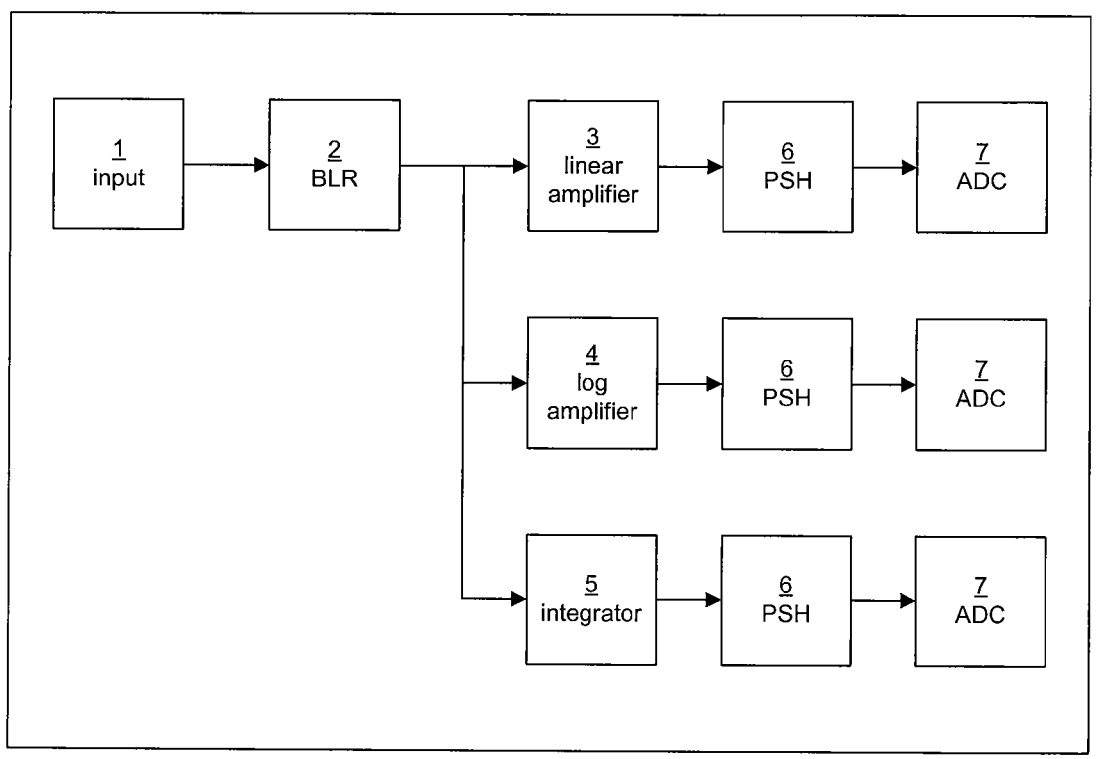
FIG. 1 is a block diagram of a design of a prior-art signal analysis system for flow cytometry.
Figure 2:
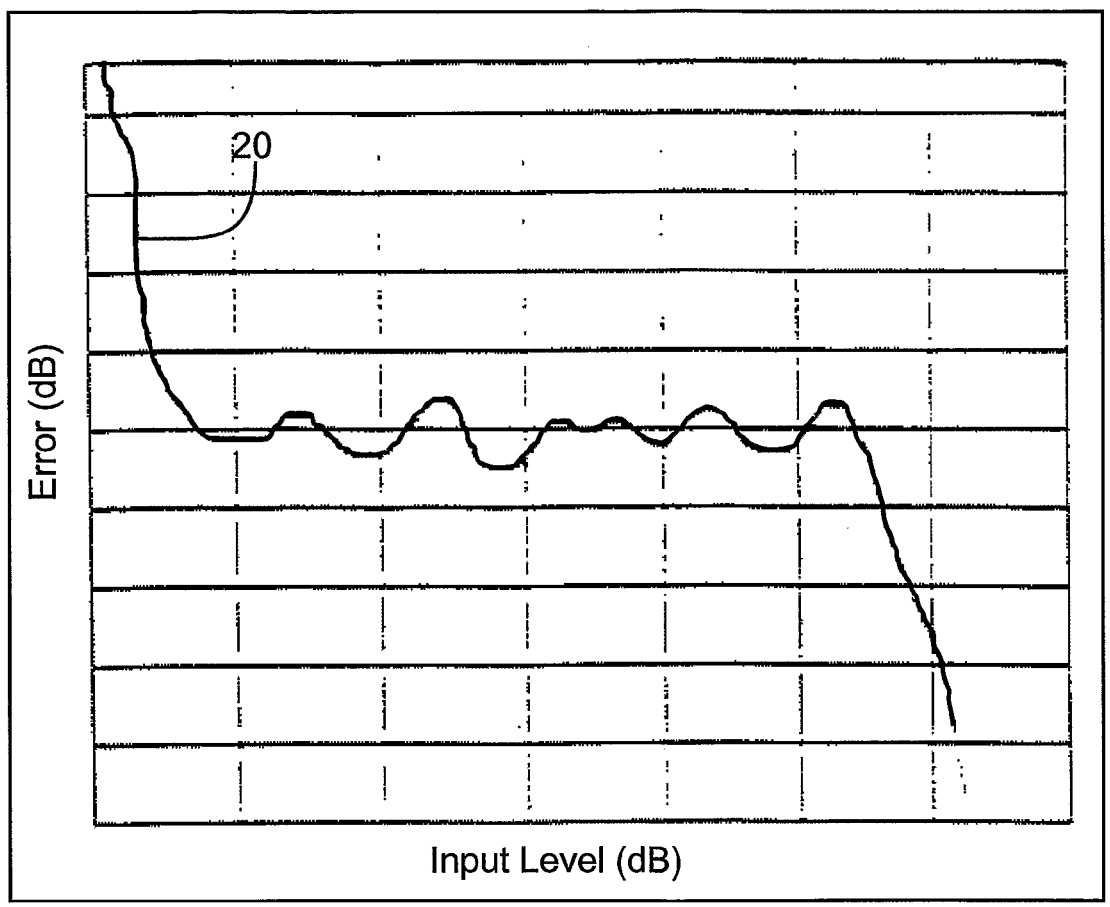
FIG. 2 is a graph showing an example of non-linearities that may exist in a logarithmic amplifier.

As mentioned above, some early systems designed to analyze the signals of a flow cytometer used an analog approach for peak determination of the linear, logarithmic, and integral values during a gated window, and then digitized the peak values at the end of the window. Referring to FIG. 1, this type of prior-art system (100) sometimes took an input signal (1), used a standard base line restoration (BLR) (2) circuit to remove DC offsets, then used a linear amplifier (3) to create the linear value, a logarithmic amplifier (4) to create the logarithmic value, and an integrator circuit (5) to calculate the integral during the window. An analog peak sample and hold circuit (PSH) (6) may then have been used to find the maximum value during the event, and this maximum value may then have been converted with an analog to digital converter (ADC) (7) to get a digital value. FIG. 2 is a graph showing an example curve (20) of some non-linearities that may have existed in a logarithmic amplifier of this prior-art system.

Figure 3:
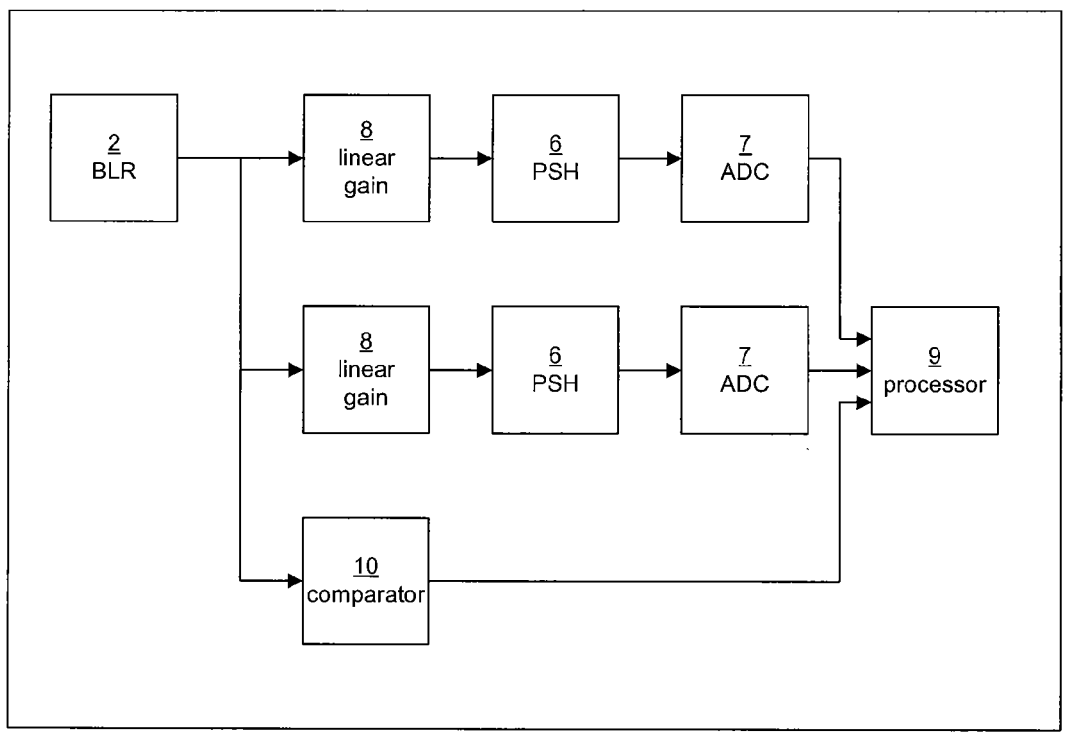
FIG. 3 is a block diagram of a second prior-art system for signal analysis for flow cytometry.

A second type of prior-art system (300), already mentioned, for signal analysis is shown in FIG. 3. This system takes the input signal (1), applies different levels of linear gain (8), determines the peak using analog PSH (6), converts the signal with an ADC (7), uses comparators (10) to determine which range to use, and then uses a processor (9) to shift the data to the appropriate place.

Figure 4:
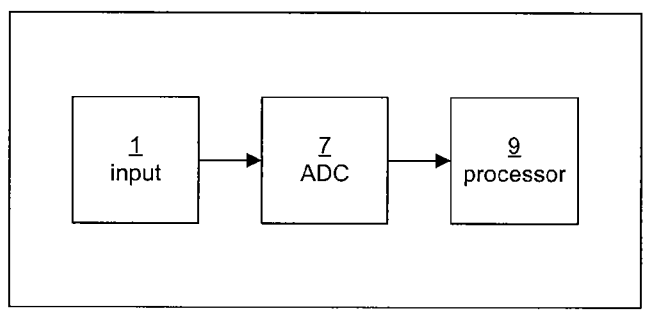
FIG. 4 is a block diagram of a third prior-art system for signal analysis for flow cytometry.

A third prior-art system (400) for signal analysis is shown in FIG. 4. This system takes the input signal (1), uses ADCs (7) to directly sample the signal, and then uses a processor (9) to perform digital PSH functionality.

Figure 7:
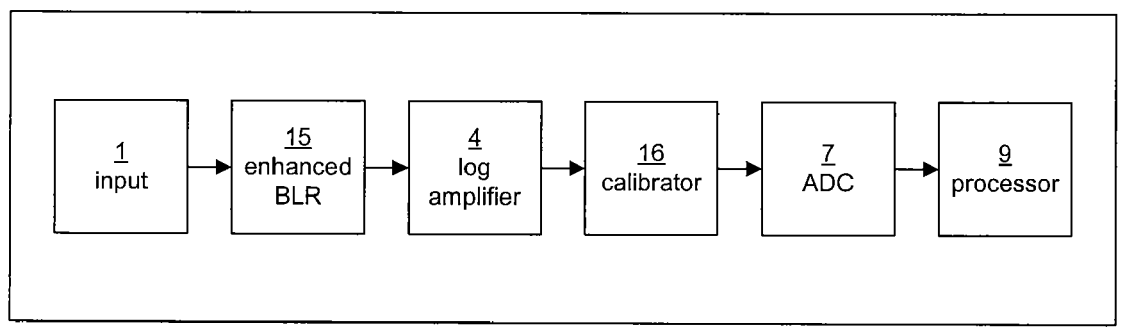
FIG. 7 is a diagram of a first preferred embodiment, in accordance with the present invention, of a system for signal analysis in flow cytometry.

Now turning to the present invention, a first preferred embodiment (700) of a method, in accordance with the present invention, for measuring and analyzing signal data in a flow cytometer, may be seen in detail in FIG. 7. Here, an input signal (1) may have any DC offset removed by an enhanced BLR (15) that may be locked during acquisition. The signal may then be transformed by a logarithmic amplifier (4), perhaps calibrated with gain and offset adjustments (16), sampled by an ADC (7), and fed to a processor (9). The processor (9) may accept one or more channels of data, with one or more processors (9) per board, and one or more boards per system. This may allow for a flexibility of overall number of channels. The processor (9) may be used to perform the digital PSH function, as well as calculate or generate any other parameters desired, or provide other needed functionality.

Figure 8:
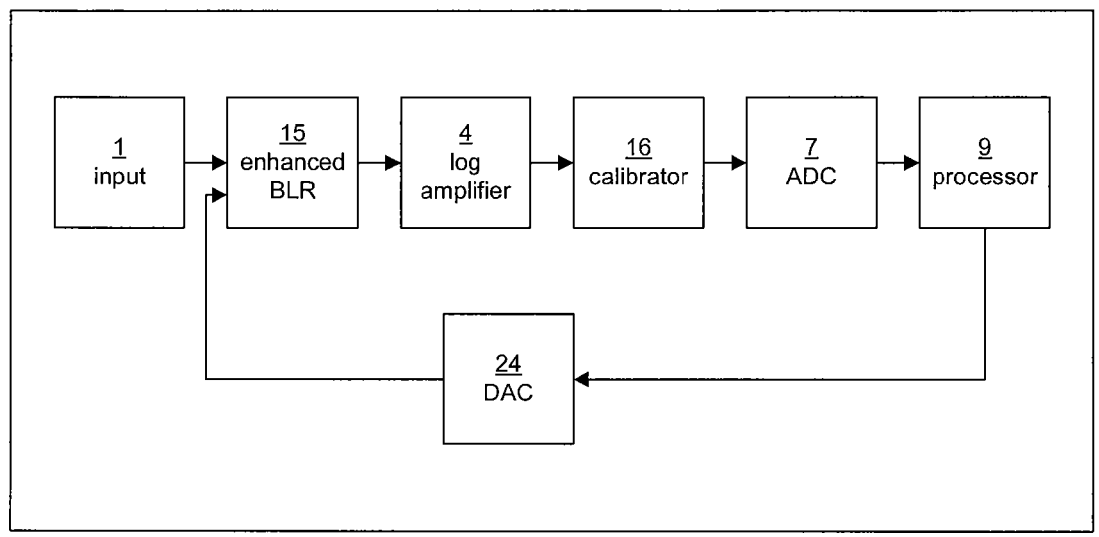
FIG. 8 is a diagram of a second preferred embodiment, in accordance with the present invention, of a system for signal analysis in flow cytometry.

A second preferred method (800), in accordance with the present invention, for measuring and analyzing signal data in a flow cytometer, is illustrated in FIG. 8. In this method, which accomplishes the enhanced BLR (15) with locking, the output of the ADC (7) may be analyzed by the processor (9), while adjusting a DC level that is summed into the input signal by the enhanced BLR (15). A digital to analog converter (DAC) (24) may be used to implement the DC voltage. When the ADC (7) output is at the correct level, the DC offset may remain fixed. In many cases, the output of the logarithmic amplifier (4) may be the absolute deviation from zero volts, so the correct level could be the minimum output of the logarithmic amplifier. By fixing the offset during acquisition, the base line may not be in jeopardy of being affected by event rate and creating error. Additionally, fine tuning can be performed digitally to further increase accuracy.

Figure 5:
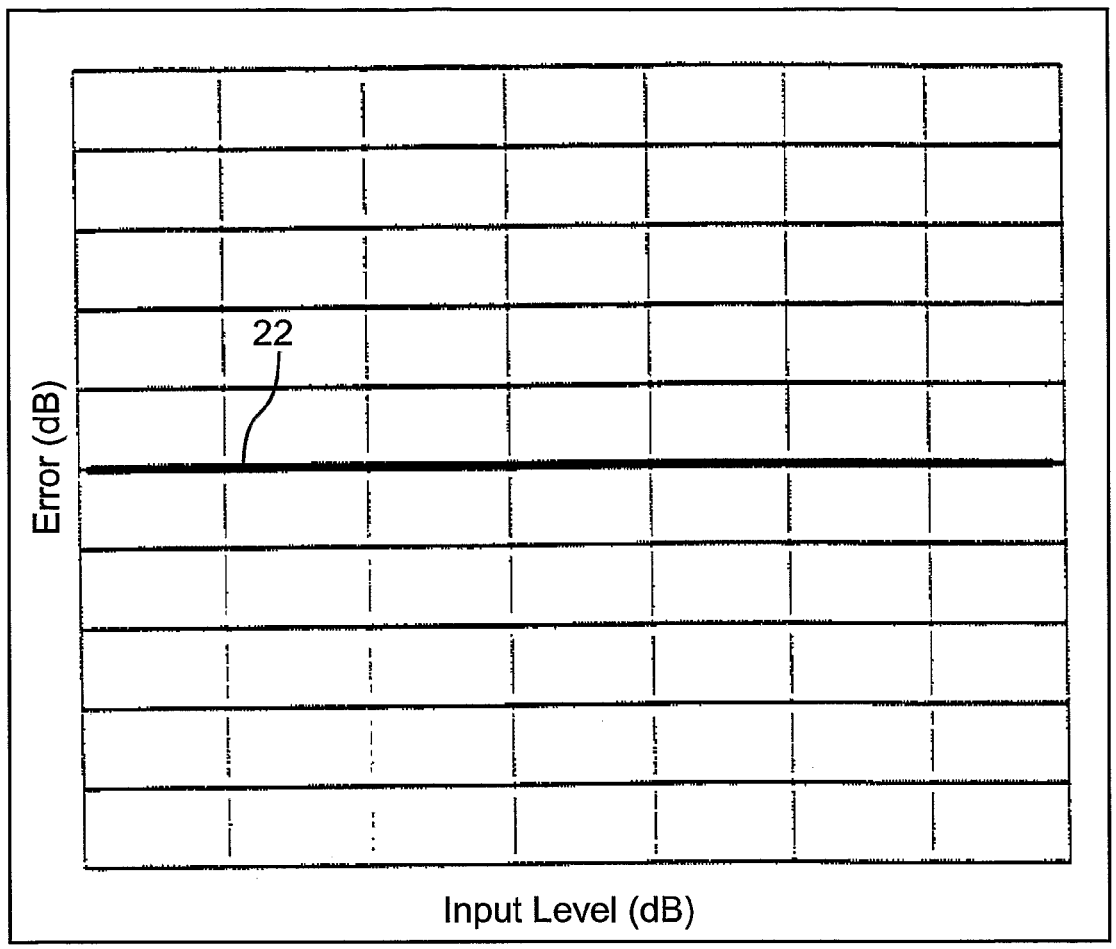
FIG. 5 is a graph showing an example of a logarithmic amplifier transfer function after compensating for non-linearity errors.

Another related preferred embodiment of a method, in accordance with the present invention, that may be used to correct for system or converter non-linearities may be to use a logarithmic amplifier (4), and then perform a calibration that measures the errors over the range of the inputs. Given a known input, the deviation from the theoretical transfer function value may be calculated. The processor (9) may then compensate the measured data to correct for the errors, perhaps producing an effective transfer function (22) with little or no error, as shown in FIG. 5. A further embodiment of the invention may be to use a look up table to change every ADC value to the corrected value. The correction table may be calculated for every channel to compensate for differences between components, channels, and boards.

Figure 6:
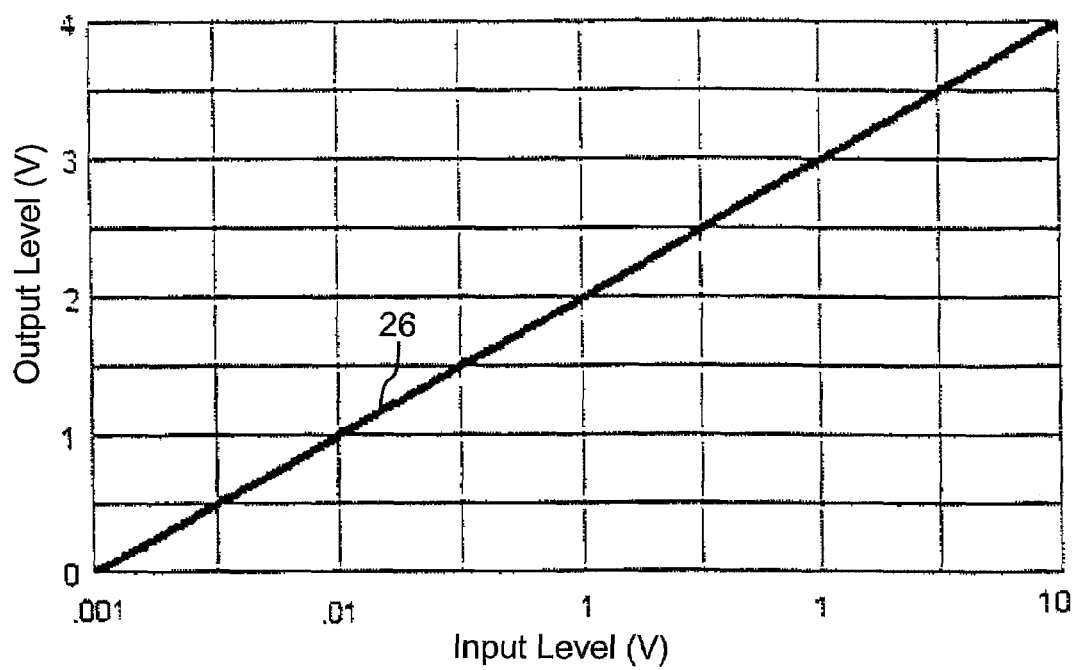
FIG. 6 is a graph showing an example of a non-linear transfer function, in this case, a logarithmic amplifier.

Another related embodiment of a method, in accordance with the present invention, that may separate digitization resolution from sampled dynamic range may use the non-linear transfer function of the logarithmic amplifier (4) to compress the dynamic range of the input signal (1). The logarithmic transfer function may convert a linear signal to an output that may be linear in dB to the input signal (1). Thus, for every decade of change in the input, the output may change a fixed amount. For example, FIG. 6 shows a logarithmic transfer function where the output changes by 1V for every 20 dB of input change. This output then may be measured or characterized at much lower resolution than would be needed for the original input signal. For example, if 12 bits were needed, a 12-bit ADC could be used. This shows a clear improvement over the 20 bits previously needed to analyze the input signal with the same resolution. By separating the required digitization resolution from the sampled dynamic range, the invention may provide greater flexibility and unbounded range for current and future analysis components. In one embodiment, a 14-bit ADC may be used to achieve high resolution sampling evenly spread over each decade of input. However, alternate configurations may be able to use much lower resolution ADCs, such as 8-bit converters.

Another embodiment, in accordance with the present invention, may use all of these individual embodiments to create a system that may have less BLR error, less conversion nonlinearity error, and more flexible and perhaps unbounded dynamic range. These embodiments individually or in collusion may create analysis electronics for flow cytometry with improved accuracy and precision for high dynamic ranges without requiring undue costs or hardware.

As can be easily understood from the foregoing, the basic concepts of the present invention may be embodied in a variety of ways. The invention involves both signal measurement and signal analysis techniques as well as devices to accomplish the appropriate signal measurements and signal analysis. In this application, the signal measurement and signal analysis techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system and both in a flow cytometry context and otherwise.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "amplifier" should be understood to encompass disclosure of the act of "amplifying"—whether explicitly discussed or not—and, conversely, were there effectively disclosure of the act of "amplifying", such a disclosure should be understood to encompass disclosure of an "amplifier" and even a "means for amplifying" Such changes and alternative terms are to be understood to be explicitly included in the description.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Patent Application or other information statement filed with the application are hereby appended and hereby incorporated by reference. However, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the signal measurement and signal analysis devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, xiii) processes performed with the aid of or on a computer as described throughout the above discussion, xiv) a programmable apparatus as described throughout the above discussion, xv) a computer readable memory encoded with data to direct a computer comprising means or elements which function as described throughout the above discussion, xvi) a computer configured as herein disclosed and described, xvii) individual or combined subroutines and programs as herein disclosed and described, xviii) the related methods disclosed and described, xix) similar, equivalent, and even implicit variations of each of these systems and methods, xx) those alternative designs which accomplish each of the functions shown as are disclosed and described, xxi) those alternative designs and methods which accomplish each of the functions shown as are implicit to accomplish that which is disclosed and described, xxii) each feature, component, and step shown as separate and independent inventions, and xxiii) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising" are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method for measuring and analyzing data contained within pulses of an analog electronic signal derived from optical measurements in a flow cytometer, the electronic signal comprising a first data channel, the method comprising the steps of:
- (a) removing a DC offset from the signal with a base line restoration circuit to obtain a base line restored signal, wherein the DC offset is locked during the pulses;
- (b) transforming the base line restored signal with a logarithmic amplifier;
- (c) sampling the transformed signal with an analog-to-digital converter so as to produce a digital signal; and
- (d) analyzing the digital signal with an electronic processor.

2. The method of claim 1, wherein the processor performs peak sample and hold analysis upon the digital signal.

3. The method of claim 1, wherein the processor further analyzes a second digital signal comprising a second data channel of the flow cytometer.

4. The method of claim 1, comprising the further step, between the transforming step (b) and the sampling step (c) of calibrating a gain of the transformed signal.

5. The method of claim 1, comprising the further steps of:
- (e) controlling a digital-to-analog converter based upon the signal analysis performed by the processor; and
- (f) inputting a DC voltage from the digital-to-analog converter to the base line restoration circuit.

6. The method of claim 1, wherein the processor calibrates for errors in the transformed signal output of the logarithmic amplifier.

7. The method of claim 6, wherein the calibration is performed using a lookup table for correcting output values of the analog-to-digital converter.

8. The method of claim 1, wherein the analog-to-digital converter samples at a lower bit resolution than is required to analyze the signal prior to the transforming step (b).

9. A system for measuring and analyzing data contained within pulses of an electronic signal derived from optical measurements in a flow cytometer, the electronic signal comprising a first data channel, the system comprising:
- a base line restoration circuit that receives and removes a DC offset from the electronic signal, wherein the DC offset is locked during the pulses;
- a logarithmic amplifier that receives the signal from the base line restoration circuit and transforms the signal;
- an analog-to-digital converter that receives the transformed signal from the logarithmic amplifier and produces a digital signal; and
- an electronic processor that receives the digital output from the analog-to-digital converter.

10. The system of claim 9, wherein the processor performs peak sample and hold analysis upon the digital signal.

11. The system of claim 9, wherein the processor further analyzes a second digital signal comprising a second data channel of the flow cytometer.

12. The system of claim 9, wherein a gain of the transformed signal is calibrated.

13. The system of claim 9, further comprising:
- a digital-to-analog converter that receives a digital signal from the processor and provides a DC voltage to the base line restoration circuit.

14. The system of claim 9, wherein the processor calibrates for errors in the transformed signal output of the logarithmic amplifier.

15. The system of claim 14, wherein the calibration is performed using a lookup table for correcting output values of the analog-to-digital converter.

16. The system of claim 9, wherein the analog-to-digital converter samples at a lower bit resolution than is required to analyze the signal prior to its being input to the logarithmic amplifier.

* * * * *

UNITED STATES PATENT AND TRADEMARK OFFICE
CERTIFICATE OF CORRECTION

PATENT NO. : 7,590,500 B2  Page 1 of 1
APPLICATION NO. : 10/587887
DATED : September 15, 2009
INVENTOR(S) : Jochum et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 239 days.

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,590,500 B2 | |
| APPLICATION NO. | : 10/587887 | |
| DATED | : September 15, 2009 | |
| INVENTOR(S) | : Jochum et al. | |

It is certified that error appears in the above-identified patent and that said Letters Patent is hereby corrected as shown below:

In drawings sheet 6 of 7, "FIG. 7 Prior Art" should be changed to --FIG. 7--.

Signed and Sealed this
Twenty-second Day of March, 2011

David J. Kappos
*Director of the United States Patent and Trademark Office*